United States Patent [19]

Miyamura

[11] 4,334,025
[45] Jun. 8, 1982

[54] NOVEL SUBSTANCE M-9337 AND PROCESS FOR PREPARING SAME

[75] Inventor: Sadao Miyamura, Niigata, Japan

[73] Assignee: SS Pharmaceutical Co., Ltd., Tokyo, Japan

[21] Appl. No.: 230,293

[22] Filed: Jan. 30, 1981

[30] Foreign Application Priority Data

Jan. 31, 1980 [JP] Japan .................................. 55-10481

[51] Int. Cl.³ .......................... C12N 1/20; C12P 7/00; A61K 35/74
[52] U.S. Cl. .................................... 435/253; 435/132; 435/169; 435/886; 424/118
[58] Field of Search ............... 435/132, 169, 253, 886; 424/118

[56] References Cited

U.S. PATENT DOCUMENTS 4,014,860 3/1977 Kakinuma et al. ............. 435/886 X

Primary Examiner—Lionel M. Shapiro
Attorney, Agent, or Firm—Oblon, Fisher, Spivak, McClelland & Maier

[57] ABSTRACT

Novel substance M-9337 obtained by culturing *Streptomyces antihaemolyticus* is effective as an antitoxic substance for neutralizing toxins discharged from streptococci, staphylococci, tetanus or the like.

4 Claims, 4 Drawing Figures (× 1000)

(× 5000)

NOVEL SUBSTANCE M-9337 AND PROCESS FOR PREPARING SAME

This invention relates to novel substance M-9337 and a process for preparing same.

Toxins discharged from streptococci, staphylococci, tetanus and the like cause a hemolytic reaction and bring about various diseases. The present inventor has made extensive studies to find out an antitoxic substance for neutralizing these toxins and, as a result, found that a novel strain belonging to the genus Streptomyces which has been isolated by the present inventor is able to produce a novel substance M-9337 capable of inhibiting the hemolytic reaction. The present invention is accomplished on the basis of the above finding.

FIG. 3 (b) is an electronmicrograph of spores of *Streptomyces antihaemolyticus* (×5,000).

Figure 1:
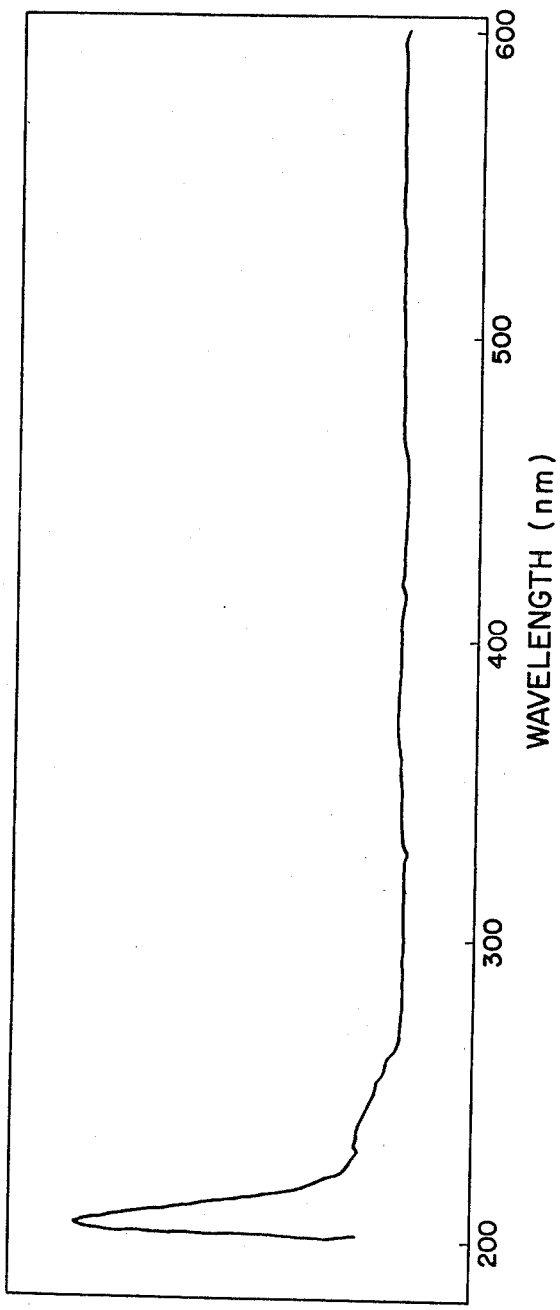
FIG. 1 is an ultraviolet absorption spectrum of substance M-9337 of this invention.

The strain capable of producing the substance M-9337 according to the invention has the following mycological properties.

(1) Morphology

Aerial hyphae are well grown in yeast-malt agar, tyrosine-agar, and oatmeal-agar media and have a diameter ranging 0.6–1.0 μm. The spore-bearing aerial hyphae is a simple one and has a wavy or spiral form, coiled once or twice. The diameter of the spiral is in the range of 4.0–5.0 μm. Conidia are oval to spherical in shape and 0.7–1.1 by 1.1–1.2 μm in size. The surface appearance is smooth as observed by an electron microscope. The number of the linkages of the spores is assumed to be above 10.

(2) Growing State in Various Media

| Medium | Growth | Aerial Hypha | Reverse | Soluble pigment |
|---|---|---|---|---|
| Sucrose-nitrate agar | poor, moist, white | after 4 days, poor, white | white | — |
| glucose-asparagine agar | good, moist, pale yellow | poor, initially, white, after 10 days, becoming pale yellow | pale yellow | pale yellow |
| glycerine-asparagine agar | good, moist, whitish grey, after 4 days, yellowish grey | poor, whitish grey | whitish grey | pale yellow |
| starch-agar | poor, pale grey, clear | moderate, white | white to pale yellow | — |
| tyrosine agar | good, moist, light grey | good, whitish grey to grey | blackish brown | blackish brown |
| nutrient agar | good, moist, grey, later becoming pale greyish yellow | poor whitish grey | pale brown | brown |
| yeast-malt agar | good, dry, rate yellow | good, whitish grey | pale brown | yellowish brown |
| oatmeal-agar | good, moist whitish grey, clear | good, ash grey, abundant | pale cream-yellow | |

(3) Physiological Properties (1) Hydrolysis of starch: −
(2) Reduction of nitrate: ±
(3) Decomposition of cellulose: −
(4) Coagulation and peptonization of skim milk: +
(5) Formation of hydrogen sulfide: ±
(6) Formation of indole: +
(7) Formation of ammonia: +
(8) VP test: +
(9) Catalase: +
(10) Formation of melanine-like pigment: +
(11) Liquefaction of gelatine: +
(12) Range of growth conditions:
   pH: 5.0~7.5
   temperature: 25°~40° C.
(13) Utilization of carbon sources: L-arabinose, D-xylose, D-glucose, D-fructose, sucrose, inositol, L-rhamnose, raffinose, and D-mannitol are utilized.

When the above-indicated mycological properties are examined with reference to ISP and Bergey's Manual of Determinative Bacteriology, the 8th edition, it has been found that the present strain belongs to the genus Streptomyces and resembles *S. robefuscus*, *S. albaduncus* and *S. naganishii*. However, the present strain differs from these species in that with *S. robefuscus*, the vegetative hyphae are tint or shade of brown in color, that with *S. albaduncus*, the utilization of sucrose is (±), and it's spore silhouette is spiny, and that *S. naganishii* makes no use of sucrose and its spore bearing aerial hyphae is not wavy or spiral. Accordingly, the present inventor recognized this strain as a novel species and called it *Streptomyces antihaemolyticus*, which was deposited at the Fermentation & Research Institute, Agency of Industrial Science and Technology, Japan, under Deposit No. 4651 (FERM-P No. 4651). This microorganism has been deposited with the American Type Culture Collection, Rockville, Md., and has the Accession Number 31801.

The substance M-9337 of the present invention is prepared, for example, by culturing the strain of *antihaemolyticus* and isolating the substance from the culture.

The cultivation of *S. antihaemolyticus* is feasible by any of methods ordinarily employed for the species belonging to the genus Streptomyces and is preferably carried out by a shaking culture using a liquid medium or a submerged culture. The medium used for the culture may be any of synthetic media, semi-synthetic media or natural media provided that nutrient sources which the strain makes use of are contained. The carbon sources are, for example, glucose, xylose, fructose, rhamnose, arabinose, sucrose, inositol, raffinose, mannitol, starch and the like and nitrogen sources are, for example, peptone, yeast extract, meat extract, ammonium chloride, soybean flour, L-asparagine and the like. When foaming takes place in a great degree during the culture, it is recommended to add an antifoamer such as silicon, a plant oil such as soybean oil, and a mineral oil such as adecanol.

In case where the culture is conducted on an industrial scale, the strain which has been pre-cultured is added to the medium and then cultured. The culture temperature is favorably in the range of 27°~35° C. and the culture time is conveniently in the range of about 2~5 days.

By this, the substance M-9337 is accumulated in the culture. The substance M-9337 is usually present in the mycelia and the culture broth, so that the culture is subjected to centrifugal separation or filtration to separate the mycelia therefrom. The substance M-9337 is separated from the mycelia and filtrate and purified by ordinary separation techniques such as, for example, a solvent extraction, precipitation, ion-exchange resin method, gel filtration, adsorption column chromatograph, dialysis, electrophoresis and the like which are used in combination.

Preferable separation and purification methods are those described hereinafter.

That is, the culture broth is separated into mycelia and a filtrate such as by centrifugal separation. Then, the filtrate is adjusted to a pH of about 3 and the resulting precipitate is collected, followed by washing with cold acetone or cold ether or lyophilizing and then extracting with a mixed solvent of chloroform and methanol (2:1) thereby obtaining crude M-9337 substance. This crude M-9337 substance is purified by a column chromatography using DEAE sephadex or silica gel to obtain pure M-9337 substance.

The thus obtained substance M-9337 of the present invention has the following physicochemical properties.

(1) Nature: Neutral (1 mg/ml: pH 6~7), white or light yellow powder.

(2) Elementary analysis:
C: 52~53%
H: 7~8%
O: 39~41%

(3) Solubility: Soluble in dimethylsulfoxide and a mixed solvent of chloroform and methanol, slightly soluble in water and methanol, and insoluble in ethyl acetate and chloroform.

(4) Color reaction: Positive with respect to anthrone, iodine, ammonium molybdate-perchloric acid and anisaldehyde reactions and negative with respect to ninhydrin and Dragendorff reagent reactions.

(5) Melting point: 170°~175° C. (decomposed)

(6) Ultraviolet absorption spectrum: As seen in FIG. 1.

Figure 2:
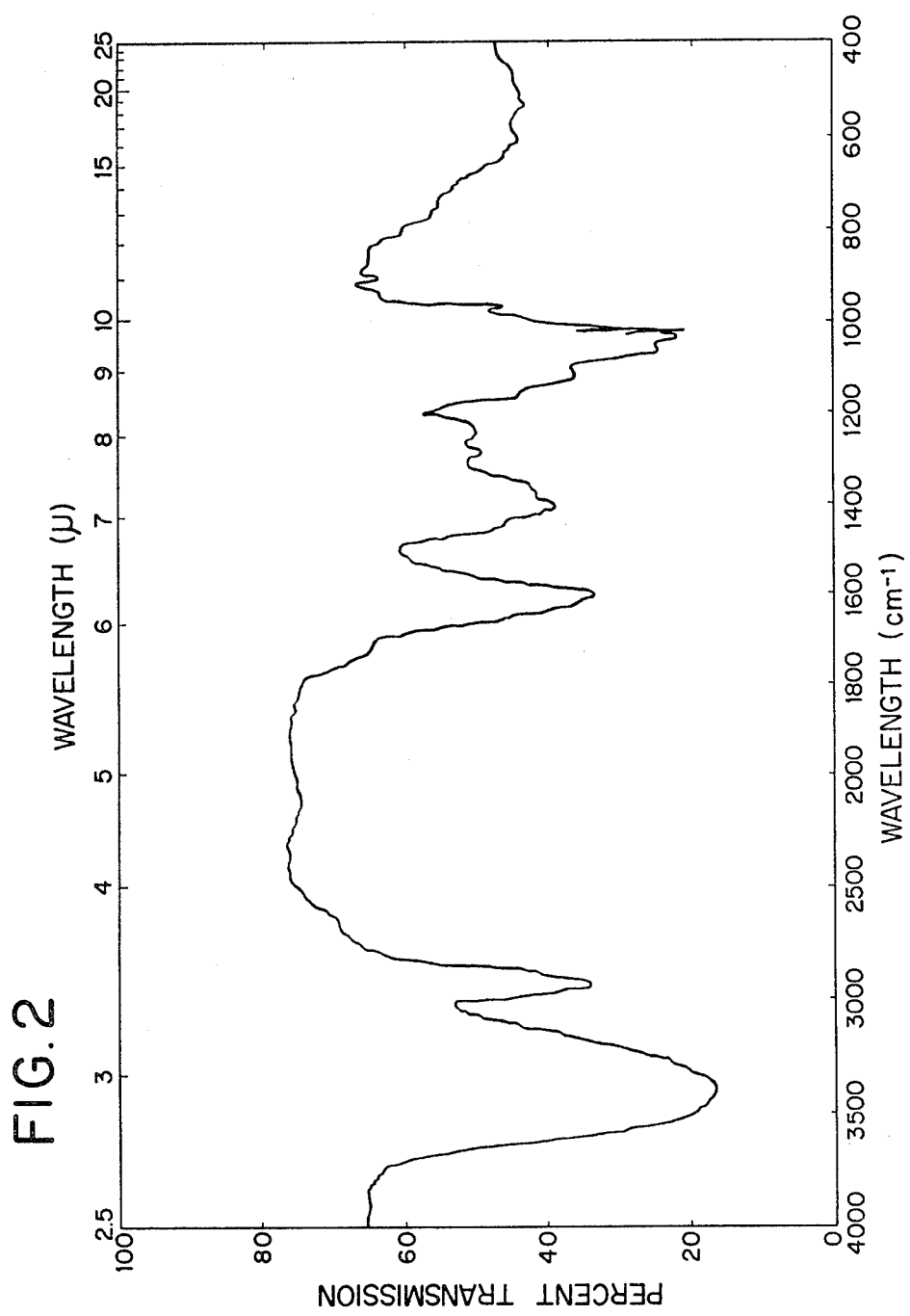
FIG. 2 is an infrared absorption spectrum of the substance M-9337.
Figure 3A:
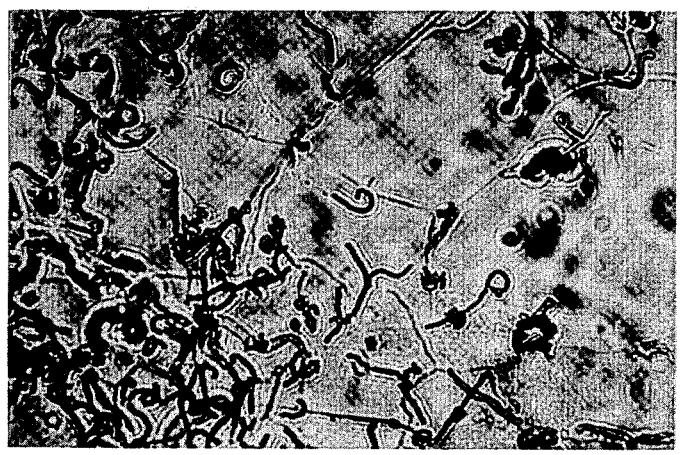
FIG. 3 (a) is a microphotograph of aerial mycelia of *Streptomyces antihaemolyticus* (×1,000)
Figure 3B:
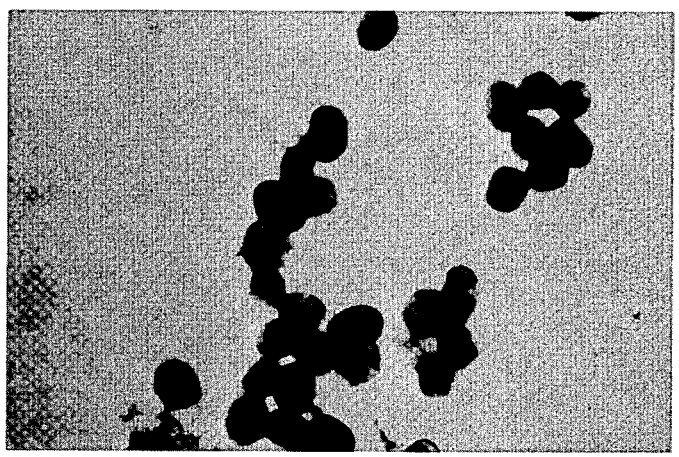

(7) Infrared absorption spectrum (KBr): As seen in FIG. 2.

(8) Thin layer chromatography:
n-propanol-water (4:1)
Rf=about 0.5
n-butanol-acetic acid-water (4:1:5)
Rf=about 0.28
toluene-formic acid-ethyl formate (5:1:4)
Rf=about 0.013
n-butanol-pyridine-water (3:2:1)
Rf=about 0.51
n-propanol-N ammonia-water (6:2:1)
Rf=about 0.41

VERIFICATION METHOD

The antihemolytic action of the M-9337 substance during the course of the culture and in the extraction and purification is tested with use of streptolysin O produced from A group hemolytic streptococcus. That is, each 1 ml of the M-9337 substance sample which has been diluted stepwise is placed in a test tube, to which is added 0.5 ml of a solution of streptolysin O (Eiken Kagaku K. K.), followed by mixing well and allowing to stand for 15 minutes in a thermostatic oven of 37° C. Thereafter, 0.5 ml of a rabbit erythrocyte suspension is added to each test tube and shaked well, followed by reacting in the thermostatic oven of 37° C. for 45 minutes to judge the presence or absence of hemolysis.

The present invention will be described in more detail by way of the following examples.

EXAMPLE 1

Shaking Flask Fermentation (A) Culture of Species

The lyophilized strain of S. antihaemolyticus (FERM Deposit No. 4651) was charged into a physiological salt solution to give a suspension and then inoculated in an agar slant medium (having a composition of glucose 10 g, L-asparagine 0.5 g, $K_2HPO_4$ 0.5 g, peptone 2.0 g, agar 15 g and purified water 1000 ml and a pH of 6.8~7.0) and cultured at 27° C. for one week. The microorganism grew prosperously with a multitude of spores growing thereon and was thus used as a species.

(B) Fermentation

A culture medium of the following composition was charged into 100 shaking flasks (Sakaguchi's flasks) with a capacity of 500 ml in an amount of 100 ml in each flask, in which two loopfuls of the spores from the medium of (A) were inoculated under germfree conditions. The flasks were placed on a reciprocating shaking machine (110 strokes, amplitude of 9 cm) and the culture was conducted at 30° C. for 96 hours.

Culture Medium: glucose 20 g, $NaNO_3$ 2.0 g, $K_2HPO_4$ 1.0 g, KCl 0.5 g, $MgSO_4$ 0.5 g, $FeSO_4$ 0.01 g, meat extract (Difco Co., Ltd.) 2.0 g, yeast extract (Difco Co., Ltd.) 2.0 g, peptone (Kyokuto) 2.0 g, defatted soybean (20 g of defatted soybean was extracted with about 1000 ml of purified water at 100° C. for 20 minutes and the resulting filtrate was used as the defatted soybean) 20 g, Adecanol LG-109 (Asahi Denka Ind. Co., Ltd.) 0.1 g, purified water 1000 ml, pH 6.8~7.0.

(C) Isolation and Purification

The culture obtained above was collected and the microorganisms were removed by a continuous centrifugal separator. About 10 l of the supernatant liquid was adjusted to a pH of 3.0 and the precipitate was collected by centrifugal separation and lyophilized. To the lyophylized matter was added a mixed solvent of chloroform and methanol (2:1) for extraction and the extract was concentrated and evaporated to dryness under reduced pressure to obtain 1.1 g of crude M-9337 substance.

40 g of silica gel (Merck Co., Ltd., 230–400 mesh) was immersed in n-hexane and immediately packed in a column tube of a diameter of 20 mm. The carrier was washed with ether and chloroform to obtain a column. Into the column was charged a solution of 500 mg of the crude M-9337 substance dissolved in a small amount of a mixed solvent of chloroform and methanol (2:1) and then eluted with a mixed solvent of chloroform and methanol (2:1). After impurities had been eluted, an active fraction containing the M-9337 substance was eluted. This fraction was collected and concentrated and evaporated to dryness under reduced pressure to obtain 80 mg of a powder. This powder was dissolved in methanol and subjected to a silica gel thin layer chromatography and developed with a mixed solvent of chloroform, methanol and water (65:25:4). A single spot of an active fraction was scraped off and extracted with methanol, followed by distilling off the solvent under reduced pressure to obtain 10 mg of M-9337 substance.

The antihaemolytic value of the substance was measured by the verification test and, as a result, it was found to be 32.0 Todd units/ml.

EXAMPLE 2

Fermentation using Jar Fermenter (A) Culture of Species

Similarly to Example 1, the culture was conducted for 48 hours to give a species.

(B) Fermentation

A culture medium of the following composition was charged into each of four jar fermenters with a capacity of 30 l in an amount of 16 l and autoclaved by a usual manner. In each fermenter was inoculated the species obtained in (A) so as to be 1.5%, followed by fermenting under the following conditions: a culture temperature was 30° C., an agitation temperature was 250 rpm/min, a flow rate of sterile air was 0.5 times by volume of the culture medium per minute, and the culture time was 96 hours. Culture Medium: glucose 20 g, NaNO$_3$ 2 g, K$_2$HPO$_4$ 1 g, KCl 0.5 g, MgSO$_4$ 0.5 g, FeSO$_4$ 0.01 g, meat extract (Difco Co., Ltd.) 2 g, yeast extract (Difco Co., Ltd.) 2 g, peptone (kyokuto) 2 g, defatted soybean (same as in Example 1) 20 g, Adecanol LG-109 (Asahi Denka Ind. Co., Ltd.) 0.1 g, purified water 1000 ml, pH 6.8~7.0.

(C) Isolation and Purification

The culture broth (about 60 l) obtained above was charged into a continuous centrifugal separator to remove the microorganisms therefrom. To the supernatant liquid was added 1 mole of hydrochloric acid to adjust its pH to 3.0 and the resulting precipitate was collected. The precipitate was washed with cold acetone and then ether, followed by extracting with a mixed solvent of chloroform and methanol (2:1) and evaporating the extract to dryness to obtain 5.1 g of crude M-9337 substance.

3.5 g of DEAE Sephadex A-50 (Pharmacia) was immersed in a mixed solvent of chloroform, methanol and 0.8 M sodium acetate (30:60:8) and packed in a column tube and the carrier was washed with chloroform-methanol-water (30:60:8) to obtain a column. Into the column was charged a solution of 100 mg of crude M-9337 substance in a small amount of 85% ethanol, followed by eluting with a mixed solvent of chloroform, methanol and 0.8 M sodium acetate (30:60:8). An active fraction was collected, from which the solvent was distilled off to obtain 14 mg of a powder. This powder was subjected to a silica gel thin layer chromatography similarly to Example 1 to obtain 1.94 mg of M-9337 substance.

This substance had an antihaemolytic value of 32.0 Todd units/ml as measured by the afore-described verification method.

EXAMPLE 3

Isolation of *Streptomyces antihaemolyticus*

Soil was collected in Niigata-shi, Niigata-ken, Japan and diluted 1,000 times with sterilized physiological saline. Then, 1 ml of the thus prepared solution was combined with 9 ml of agar culture medium for isolation, whose composition is defined below, and placed in a sterilized petri dish and cultured for 5 days at 28° C.

| Agar culture medium for isolation (I) | Composition |
| --- | --- |
| starch | 10 g |
| peptone | 2 g |
| NH$_4$Cl | 2 g |
| K$_2$HPO$_4$ | 15 g |
| agar | 15 g |
| water | 1,000 ml |
| pH 6.8 ~ 7.0 | |

Colonies resulting from the above cultivation was transferred by a platinum spatula onto a slant agar culture medium (II), whose composition is described below, and cultured for 3 days at 28° C.

| Slant agar culture medium (II) | Composition |
| --- | --- |
| glucose | 10 g |
| peptone | 2 g |
| L-asparagine | 0.5 g |
| K$_2$HPO$_4$ | 0.5 g |
| agar | 15 g |
| water | 1,000 ml |
| pH 6.8 ~ 7.0 | |

One platinum spatula scoop of the microorganism grown on the slant culture medium by the above cultivation was diluted 10,000 times with physiological saline. One milliliter of the thus-diluted microorganism was mixed with 9 ml of the agar culture medium for isolation (I) and cultured in a sterilized petri dish for 5 days at 28° C. It was visually and microscopically confirmed that no differences were observed among resultant colonies.

Among the above-described colonies ten colonies were inoculated individually onto slant agar culture media (II), and cultured for 3 days at 28° C. It was visually and microscopically confirmed that the microorganisms grown on the ten slant culture media (II) are identical to one another. It was also confirmed that those microorganisms exhibited same characteristics on each of the above culture media and physiological properties, which are described above.

As a result of the above experiments, it was found that the microorganism cultured in each of the 10 culture media belongs to a same strain of microorganisms separated in the pure form from the nature.

To the microorganism cultured above in the pure form on the slant agar culture medium (II), was added as a protective agent 10% skim milk to prepare a suspension of spore on the slant agar culture medium (II). The suspension of spore was separately filled by about 1 ml into ampules for lyophilization. The lyophilization was conducted by rapidly freezing the ampules containing the suspension of the spore in dry ice-acetone, placing the thus-frozen ampules in a lyophilizer and then lowering its vacuum level below 0.03 torr. After storing thus-obtained lyophilized microorganism (sample) for 3 months, the ampules were opened and the microorganism was transferred by a sterilized mini-spatula into sterilized test tubes, and added with a reviving solution (an aqueous solution containing 1% of glucose and 1% of yeast extract). After allowing the test tubes to stand for at least 1 hour, the characteristics and physiological properties of the microorganism was investigated on each of the culture media (I) and (II). As a result, no differences were observed between the microorganism before the lyophilization (sample) and that cultured newly.

A lyophilization and revival of the above microorganism were alternatingly repeated every month five times in total. The characteristics on the culture media and physiological properties of the resultant microorganism were investigated but no changes were observed. Accordingly, it has been proven that the microorganism of this invention can reproduce the exactly same results through its successive cultivation.

I claim:

1. A substance M-9337 having the following properties:
   (1) Nature: Neutral (1 mg/ml: pH 6–7), white to light yellow powder;
   (2) Elementary analysis:
      C ... 52–53%
      H ... 7–8%
      O ... 39–41%;
   (3) Solubility: Soluble in dimethylsulfoxide and a mixed solvent of chloroform and methanol, slightly soluble in water and methanol, and insoluble in ethyl acetate and chloroform;
   (4) Color reaction: Positive with respect to anthrone, iodine, ammonium molybdate-perchloric acid, and anisaldehyde reactions and negative with respect to ninhydrin and Dragendorff reagent reactions;
   (5) Melting point: 170°–175° C. (decomposed);
   (6) Ultraviolet absorption spectrum: As seen in FIG. 1;
   (7) Infrared absorption spectrum (KBr): As seen in FIG. 2; and
   (8) Thin layer chromatography:
      n-propanol-water (4:1)
         Rf=about 0.5
      n-butanol-acetic acid-water (4:1:5)
         Rf=about 0.28
      toluene-formic acid-ethyl formate (5:1:4)
         Rf=about 0.013
      n-butanol-pyridine-water (3:2:1)
         Rf=about 0.51
      n-propanol-N ammonia-water (6:2:1)
         Rf=about 0.41.

2. A process for preparing a substance M-9337 characterized by culturing a substance M-9337-producing strain belonging to the genus Streptomyces and collecting the substance M-9337 from the culture.

3. A process according to claim 2, wherein the substance M-9337-producing strain belonging to the genus streptomyces is *Streptomyces antihaemolyticus FERM P-No.* 4651 (ATCC No. 31801).

4. A biologically pure culture of *Streptomyces antihaemolyticus FERM P-No.* 4651 (ATCC No. 31801) said culture being capable of producing the substance M-9337.

* * * * *